United States Patent [19]
Schmidt et al.

[11] Patent Number: 5,792,613
[45] Date of Patent: Aug. 11, 1998

[54] METHOD FOR OBTAINING RNA APTAMERS BASED ON SHAPE SELECTION

[75] Inventors: Francis J. Schmidt, Columbia, Mo.; Bongrae Cho, Chung-Buk, Rep. of Korea; Hugh B. Nicholas, Jr., Pittsburgh, Pa.

[73] Assignee: The Curators of The University of Missouri, Columbia, Mo.

[21] Appl. No.: 662,335

[22] Filed: Jun. 12, 1996

[51] Int. Cl.$^6$ .............................. C12Q 1/68; C12N 15/11
[52] U.S. Cl. ........................................ 435/6; 536/23.1
[58] Field of Search .......................... 435/6, 91.1, 91.34; 536/23.1

[56] References Cited

PUBLICATIONS

Schmidt et al. Annals. N.Y. Acady. Scic. vol. 782 May 15, 1996, pp. 526–533.

D. P. Bartel et al., "Isolation of New Ribozymes from a Large Pool of Random Sequences", *Science*, 261, 1411–18 (1993).

R. T. Batey et al., "Preparation of Isotopically Labeled Ribonucleotides for Multidimensional NMR Spectroscopy of RNA", *Nucl. Acids Res.*, 20, 4515–23 (1992).

E. H. Blackburn, "Telomerase", in R. F. Gesteland, et al., eds., *The RNA World*, Cold Spring Laboratory Press, Cold Spring, NY, 557–76 (1993).

E. H. Blackburn, "Telomeres: Structure and Synthesis", *J. Biol. Chem.*, 265, 5919–5921 (1990).

L. C. Bock et al., "Selection of Single–stranded DNA Molecules that Bind and Inhibit Human Thrombin", *Nature*, 355, 564–566 (1992).

S. Brenner et al., "Encoded Combinatorial Chemistry", *Proc. Nat. Acad. Sci., USA*, 89, 5381–83 (1992).

J. M. Burke et al., "In vitro Selection and Evolution of RNA: Application for Catalytic RNA, Molecular Recognition, and Drug Discovery", *FASEB Journal*, 7, 106–112 (1993).

V. Campuzano et al., "Friedreich's Ataxia: Autosomal Recessive Disease Caused by an Intronic GAA Triplet Repeat Expansion", *Science*, 271, 1423–1427 (1996).

D. C. Capaldi et al., "Use of the Fpmp and Related Protecting Groups in Oligoribonucleotide Synthesis: Stability of Internucleotide Linkages to Aqueous Acid", *Nucl. Acids Res.*, 22, 2209–16 (1994).

M. Chamorro et al., "An RNA Pseudoknot and an Optimal Heptameric Shift Site are Required for Highly Efficient Ribosomal Frameshifting on a Retroviral Messenger RNA", *Proc. Nat. Acad. Sci., USA*, 89, 713–717 (1992).

K. Y. Chang et al., "Characterization of a Kissing Hairpin Complex Derived from the Human Immunodeficiency Virus Genome", *Proc. Nat. Acad. Sci, USA*, 91, 8705–8709 (1994).

X. Chen et al., "Hairpins are Formed by the Single DNA Strands of the Fragile X Triplet Repeats: Structure and Biological Implications",*Proc. Natl. Acad. Sci., USA*, 92, 5199–5203 (1995).

J. H. Chen et al., "Synthesis from DNA of a Molecule with the Connectivity of a Cube", *Nature*, 350, 631–33 (1991).

C. Cheong et al., "Solution Structure of an Unusually Stable RNA Hairpin 5'GGAC(UUCG) GUCC", *Nature*, 346, 680–82 (1990).

B. Cho et al., "Selection of Aptamer RNAs that Bind to RNA Structural Motifs", Abstract FASEB workshop, (Fall, 1994).

S. C. Darr et al., "Contributions of Phylogenetically Variable Structural Elements of the Function of the Ribozyme Ribonuclease P.", *Biochemistry*, 31, 328–333 (1992).

A. D. Ellington et al., "In vitro Selection of RNA Molecules that Bind Specific Ligands", *Nature*, 346, 818–822 (1990).

J. Feigon "NMR Studies of RNA Aptamers for Biological Cofactors", Abstract *National Science Foundation*, grant #9506913, (FY–1997).

D. F. Feng et al., "Progressive Sequence Alignment as a Prerequisite to Correct Phylogenetic Trees", *J. Mol. Evol.*, 25, 351–360 (1987).

A. M. Gacy et al., "Trinucleotide Repeats that Expand in Human Disease Form Hairpin Structures In Vitro", *Cell*, 81, 533–40 (1995).

R. Green et al., "In vitro Genetic Analysis of the Hinge Region Between Helical Elements P5–P4–P6 and P7–P3–P8 in the sunY Group I self splicing Intron", *J. Mol. Biol.*, 235, 140–55 (1994).

R. Green et al., "Selection of a Ribozyme that Functions as a Superior Template in a Self–copying Reaction", *Science*, 258, 1910–1915 (1992).

E. S. Haas et al., "Long–Range Structure in Ribonuclease P RNA", *Science*, 254, 853–856 (1991).

M. L. Herlocher et al., "Molecular and Biological Changes in the Cold–adapted Master Strain A/AA/60 (H2N2) Influenza Virus", *Proc. Nat. Acad. Sci. USA*, 90, 6032–37 (1993).

M. Illangasekare et al., "Aminoacyl–RNA Synthesis Catalyzed by an RNA", *Science*, 267, 643–47 (1995).

T. Jacks, "Translational Suppression in Gene Expression in Retroviruses and Retrotransposons", *Current Topics in Microbiology and Immunology*, 157, 93–124 (1990).

J. A. Jaeger et al., "Determination of RNA Structure and Thermodynamics", *Ann. Rev. Biochem.*, 62, 255–87 (1993).

L. Jaeger et al., "Involvement of a GNRA Tetraloop in Long–range RNA Tertiary Interactions", *J. Mol. Biol.*, 236, 1271–1276 (1994).

J. X. Khym "The Reaction of Methylamine with Periodate–oxidized Adenosine–5'–phosphate", *Biochemistry*, 2, 344–350 (1963).

(List continued on next page.)

*Primary Examiner*—John L. LeGuyader
*Attorney, Agent, or Firm*—Schwegman, Lundberg, Woessner & Kluth, P.A.

[57] ABSTRACT

RNA molecules are selected from a random sequence library for their ability to bind to a selecting nucleic acid structural element. Selection of RNA aptamers with extensive Watson-Crick complementarity to the nucleic acid ligand is precluded by inclusion of a blocking oligodeoxynucleotide in the binding phase of the selection protocol.

24 Claims, 5 Drawing Sheets

OTHER PUBLICATIONS

D. Labuda et al., "Mechanism of Codon Recognition by Transfer RNA studied with Oligonucleotides Larger than Triplets", *Nucl. Acids Res.*, 13, 3667–83 (1985).

D. E. Lawrence et al., "Detecting Subtle Sequence Signals: A Gibbs Sampling Strategy for Multiple Alignments", *Science*, 262, 208–214 (1993).

N. Lehman et al., "Evolution in vitro of an RNA Enzyme with Altered Metal Dependence", *Nature*, 361, 182–185 (1993).

F. Liu et al., "Differential Evolution of Substrates for an RNA Enzyme in the Presence and Absence of its Protein Cofactor", *Cell*, 77, 1093–1100 (1994).

J. R. Lorsch et al., "In vitro Evolution of New Ribozymes with Polynucleotide Kinase Activity", *Nature*, 371, 31–36 (1994).

W. H. McClain et al., "Model Substrates for an RNA Enzyme", *Science*, 238, 527–530 (1987).

J. F. Milligan et al., "Oligoribonucleotide Synthesis Using T7 RNA Polymerase and Synthetic DNA Templates", *Nucl. Acids Res.*, 15, 8738–98 (1987).

J. F. Milligan et al., "Synthesis of Small RNAs Using T7 RNA Polymerase", *Methods in Enzymology*, 180, 51–62, (1989).

D. P. Morse et al., "Sequences Encoding the Protein and RNA Components of Ribonuclease P from Streptomyces bikiniensis var. zorbonensis", *Gene*, 117, 61–66 (1992).

D. P. Morse et al., "Suppession of Loss–of–Function Mutations in *Escherichia coli* Ribonuclease P RNA (M1 RNA) by a Specific Base–pair Disruption", *Jour. Mol. Biol.* 230, 11–14 (1993).

E. P. Nikonowicz et al., "Preparation of $^{13}$C and $^{15}$N Labelled RNAs for Heteronuclear Multi–dimensional NMR Studies", *Nucl. Acids Res.*, 20, 4507–13 (1992).

H. F. Noller, "On the Origin of the Ribosome: Coevolution of Subdomains of tRNA and rRNA.", in R. F. Gesteland et al., eds., *RNA World*, Cold Spring Harbor Laboratory, Cold Spring Harbor, NY, 137–56 (1993).

N. Pace et al., "Evolutionary Perspective of the Structure and Function of Ribonuclease P, a Ribozyme", *J. Bacteriol.*, 177, 1919–28 (1995).

T. Pan et al.,"In vitro Selection of RNAs that Undergo Autolytic Cleavage with Pb2+", *Biochemistry*, 31, 3887–95 (1992).

G. Paolella et al., "Nuclease Resistant Ribozymes with High Catalytic Activity", *EMBO Journal*, 11, 1913–19 (1992).

N. T. Parkin et al., "Human Immunodeficiency Virus type 1 gag–pol Frameshifting is Dependent on Downstream mRNA Secondary Structure: Demonstration by Expression In Vivo", *J. Virol.*, 66, 5147–51 (1992).

D. Pei et al., "A Combinatorial Approach Toward DNA Recognition", *Science*, 253, 1408–11 (1991).

R. Poljak."An Idiotype—Anti–idiotype Complex and the Structural Basis of Molecular Mimicking", *Proc. Nat. Acad. of Sci., USA*, 91, 1599–1600 (1994).

J. R. Prudent et al., "Expanding the Scope of RNA Catalysis", *Science*, 264, 1924–27 (1994).

A. M. Pyle et al., "Ribozyme Recognition of RNA by Tertiary Interaction with Specific Ribose 2'OH Groups", *Nature*, 350, 628–31 (1991).

R. Ramamoorthy et al., "Transcript Hairpin Structures are not Required for RNA Polymerase Pausing in the Gene Encoding the *E. coli* RNase P RNA, M1 RNA", *FEBS Letters*, 295, 227–29 (1991).

K. Randerath et al., "[$^3$H] Borohydride: a Versatile Reagent for the Analysis of tRNA — Methods and Applications.", in P. R. Schimmel et al., eds., *Transfer RNA: Structure, Properties and Recognition*, Cold Spring Harbor Laboratory Press, Cold Spring Harbor, NY, 43–58 (1979).

D. D. Richman, "HIV Drug Resistance", *Ann. Rev. Pharmocol.*, 33, 149–164 (1993).

F. J. Schmidt, "Ribobodies: RNA Aptamers selected for Recognition of an RNA Structural Motif", *Abstract for the Gordon Conference*, (June 1995).

F. J. Schmidt et al., "Ribobodies: RNA Aptamers that Recognize a Structural Motif in RNAse P", Abstract, *RNA '96 The First Annual Meeting of the RNA Society*, (May 26–Jun. 2, 1996).

F. J. Schmidt, et al., "RNA Aptamers Recognizing RNA Structural Elements", Summary of National Science Foundation Grant Number DMB931939, (1993).

F. J. Schmidt, et al., "RNA Libraries and RNA Recognition", Abstract Engineering Fundamentals Conference Recombinant DNA Biotechnology III, Deuville, France, (Oct. 16–21, 1994).

F. J. Schmidt, "Selection of RNAs Inhibiting HIV GAG–POL Frameshifting", Abstract, *National Institute of Allergy and Infectious Diseases*, grant 1R41AI38610–01, (FY–1996).

F. J. Schmidt et al., "Transfer Ribonucleic Acid Biosynthesis", *J. Biol. Chem.*, 251, 2440–45 (1976).

J. K. Scott, et al., "Searching for Peptide Ligands with an Epitope Library", *Science*, 249, 386–390 (1990).

D. Sen, et al., "A Sodium–Potassium Switch in the Formation of Four–Stranded G4–DNA", *Nature*, 344 410–414 (1990).

W. I. Sundquist, et al., "Telomeric DNA Dimerizes by Formation of Guanine Tetrads Between Hairpin Loops", *Nature*, 342, 825–829 (1989).

D. C. Taylor, et al., "Aptamer Recognition for RNA Motif in Native Context", Abstract, *RNA '96 The First Annual Meeting of the RNA Society*, (May 28–Jun. 2, 1996).

C. Tuerk, et al., "Systemic Evolution of Ligands by Exponential Enrichment: RNA Ligands to Bacteriophage T4 DNA Polymerase", *Science*, 249, 505–510 (1990).

D. S. Waugh, et al. "The Design and Catalytic Properties of a Simplified Ribonuclease P RNA", *Science*, 244, 1569–71 (1989).

M. L. Zapp, et al., "Small Molecules that Selectively Block RNA Binding of HIV–1 Rev Protein Inhibit Rev Function and Viral Production", *Cell*, 74, 969–978 (1993).

M. Zucker, "On Finding All Suboptimal Folding of an RNA Molecule", *Science*, 244, 48–52 (1989).

FIG. 3A

```
              1                                                    50
g18_01.seg    ..................................................
g18_04.seg    ..................................................
g18_10.seg    .....................t............................
g18_11.seg    ................................t.................
g18_12.seg    .....................t............................
a_07.seg      ..............................................a...
g12_3.seg     ..........................................t.......
CONSENSUS     CCGAAGCATT CCGGGCGTAGG GGTCTGTGCG CAAAACCATC GGCCCGGGTG
```

FIG. 3B

```
              1                                                    50
g18_06.seg    TTCCTTAGGG GTTCAGTTGT TTCGCGCATG AACGGCATCA GTGCACCGTG
g18_09.seg    AGTTGATCGA GCGTGTTAGT TCTCCAATCT CTGTGTAGCG TGGAGCTGGG
```

METHOD FOR OBTAINING RNA APTAMERS BASED ON SHAPE SELECTION

STATEMENT OF GOVERNMENT RIGHTS

This invention was made with the support of the U.S. Government under Grant No. DMB931939 from the National Science Foundation, and Grant No. LM05513 from the National Institutes of Health. The U.S. Government has certain rights in the invention.

BACKGROUND OF THE INVENTION

RNA—RNA recognition is a feature of numerous molecular biological processes including translation, post-transcriptional regulation, and the action of ribozymes. Most known nucleic acid recognition processes utilize Watson-Crick base pairing; however, other forms of nucleic acid interaction are known. For example, the ribozyme ribonuclease P (RNase P) recognizes its pre-tRNA substrate largely by way of shape selection (W. H. McClain et al., *Science* 238 527–530 (1987); F. Liu et al., *Cell*, 77, 1093–1100 (1994)). Even when base pairing is used to select RNAs for interaction, e.g., during catalysis by the Tetrahymena Group I ribozyme, tertiary interactions within the ribozyme and between ribozyme and substrate affect the strength and specificity of Watson-Crick base pairing (A. M. Pyle et al., *Nature*, 350 628–631, (1991)).

Combinatorial RNA selection experiments have been employed to isolate synthetic RNA species capable of recognizing a variety of molecules, including small molecules, proteins and metabolic cofactors. Tuerk et al. (*Science*, 249, 505–510 (1990)), pioneered the process of systematic evolution of ligands by selective enrichment (SELEX), wherein successive steps of affinity purification and amplification allow the propagation and eventual isolation of specific binding RNA molecules, termed aptamers. SELEX was designed for the purification of nucleic acid ligands exhibiting high affinity for any given protein that binds nucleic acids. In this procedure, a pool of completely random RNA molecules is allowed to bind a purified protein that is attached to a solid support. After removing unbound (i.e., free) RNA molecules, the bound RNA molecules are separated from the protein, amplified using polymerase chain reaction to yield double-stranded cDNA, then in vitro translated into RNA. This amplified population of RNA molecules, slightly enriched for sequences that bind the protein, is subjected to the next cycle of enrichment. The cycle is repeated several times to produce a selected population of RNA molecules highly enriched for those with the highest affinity for the protein.

A. D. Ellington et al. (*Nature*, 346, 818–822 (1990)) extended the use of SELEX to obtain nucleic acid molecules (oligo-A sequences) having Watson-Crick complementarity to a target oligonucleotide (oligo-dT). D. Pei et al. (*Science*, 253, 1408–1411 (1991)), showed that this process could be used to obtain oligopyrimidine sequences capable of triple helix (triplex) formation by using a DNA duplex to bind a random nucleic acid library.

Further refinement of the selection schemes has allowed the isolation of autocatalytic and catalytic nucleic acid species (J. R. Prudent et al., *Science*, 264, 1924–1927 (1994)), and RNAs capable of self-aminoacylation (M. Illangasekare et al., *Science*, 267, 643–647 (1995)). Techniques of combinatorial selection have also been applied to define features important for substrate recognition by RNase P wherein selected RNA substrates binding to a target RNase P were found to resemble naturally occurring RNA substrates for RNase P RNA (F. Liu et al., *Cell*, 77, 1093–1100 (1994)).

Selections reported in the literature for nucleic acid interactions have thus resulted in the selection of RNA aptamers utilizing well-characterized modes of sequence recognition, such as Watson-Crick base-pairing and Hoogsteen base pairing (i.e., triple helix formation). It is known from studies on catalytic and other RNAs, however, that both inter- and intramolecular nucleic acid interactions can occur by mechanisms other than duplex- or triplex-type base pairing. Yet, no in vitro selection method based upon interactions of this nature exists in the art.

There is, therefore, a need for a method of identifying, isolating and characterizing RNA molecules that bind nucleic acids, particularly those that bind other RNA molecules, which method employs a mechanism that does not involve duplex- or triplex-type base pairing.

SUMMARY OF THE INVENTION

The present invention provides a method for selecting an RNA aptamer that binds a nucleic acid molecule by way of shape recognition. The method effectively distinguishes shape-recognizing RNA aptamers from RNA aptamers that bind the nucleic acid molecule primarily by way of base pairing interactions, such as Watson-Crick interactions.

Selection of RNA aptamers that preferentially bind the structural element of a selecting nucleic acid molecule by way of shape recognition rather duplex- or triplex-type base pairing interactions is accomplished by pretreating a large RNA population with a sufficient quantity of blocking oligodeoxynucleotide to preclude potential basepairing interactions between RNA molecules in the population and the selecting nucleic acid molecule. The nucleotide sequences of the blocking oligodeoxynucleotide and the selecting nucleic acid molecule are the same, except that the oligodeoxynucleotide (a DNA) has thymine at nucleotide positions that contain uracil when the selecting nucleic acid molecule is an RNA molecule. Because it is DNA, the blocking oligodeoxynucleotide is not likely to form the structural element characteristic of the sequence of the selecting RNA molecule, and will therefore pair with complementary RNA molecules in solution. The consequent formation of DNA-RNA duplexes effectively removes these RNA molecules from the selection process. Where the selecting nucleic acid is DNA, it is presumed that the blocking oligodeoxynucleotides spend sufficient time in a linear form to permit the formation of DNA-RNA duplexes with complementary RNAs in the RNA population.

After pretreatment with the blocking oligodeoxynucleotide, the candidate RNA population is subjected to a selection process whereby it is first contacted with the selecting nucleic acid molecule to allow noncovalent binding of the RNA aptamer to the structural element of the selecting nucleic acid molecule. The resulting RNA aptamer:nucleic acid molecule complex is then separated from the remaining free RNA molecules, after which the complex is dissociated. The selected RNA population is thereby enriched for RNA aptamers that bind the selecting nucleic acid molecule by way of shape recognition.

The nucleotide sequences of RNA molecules present in the selected RNA population may be determined at any time using genetic engineering methods known in the art, and successive rounds of selection are carried out until at least one characteristic sequence motif becomes apparent.

Specifically, the present invention provides a method for obtaining an RNA aptamer that binds a structural element of a selecting nucleic acid molecule comprising:

(a) contacting an RNA population suspected of containing an RNA aptamer that binds the structural element with a blocking oligodeoxynucleotide having a nucleotide sequence equivalent to the nucleotide sequence of the structural element, for a time and under buffer conditions sufficient to allow duplex formation between the blocking oligodeoxynucleotide and a member of the RNA population having a sequence complementary to that of the blocking oligodeoxynucleotide, to yield a candidate RNA population comprising free RNA molecules and blocked RNA-oligodeoxynucleotide duplexes;

(b) contacting the candidate RNA population with the selecting nucleic acid molecule for a time and under buffer conditions sufficient to allow the formation of a noncovalent complex comprising bound RNA and the selecting nucleic acid molecule;

(c) separating non-complexed RNA from the noncovalent complex;

(d) separating the bound RNA from the selecting nucleic acid molecule of the noncovalent complex to yield a selected RNA population; and (e) repeating steps (b) through (d), wherein step (b) in the repetition is performed on the selected RNA population, for a number of cycles sufficient to yield a selected RNA population comprising a detectable amount of RNA aptamer.

The RNA population used as the starting material can be a synthetic RNA library, preferably randomized, or naturally occurring RNA population. After each round of selection, the selected RNA population, enriched for the RNA aptamer of interest, is preferably reverse transcribed to cDNA, amplified, then transcribed into RNA before beginning the next round of selection. Prior to transcription, the sequence of the reverse transcribed cDNA may be determined directly, or the cDNA may cloned into a suitable vector, transformed into a suitable cell line, amplified and subjected to DNA sequencing according to methods well known in the art.

The nucleic acid structural elements recognized by RNA aptamers selected according to the invention include those formed by any type or combination of secondary or tertiary intramolecular interactions, such as hairpins, stem-loops, bulge-loops, pseudoknots, tetraplex structures, and G-quartets.

The blocking oligodeoxynucleotides used to pretreat the RNA population before subjecting it to the selection process can include overlapping oligodeoxynucleotides, each having a nucleotide sequence equivalent to a portion of the nucleotide sequence of the structural element, such that each nucleotide position in the structural element corresponds to a nucleotide position in at least one of the overlapping oligodeoxynucleotides.

Selection of RNA aptamers according to the present invention is preferably carried out using affinity chromatography, wherein the selecting nucleic acid molecule is affixed to a column matrix. Preferably, a preselection procedure is used to remove any members of the RNA population that bind nonspecifically to the column matrix. After formation of the RNA aptamer:selecting nucleic acid complex, bound aptamer RNA can be eluted from the column by either chelating the $Mg^{2+}$ that stabilizes the complexes, or by supplying a sufficient quantity of free competing nucleic acid such that the bound RNA aptamers are displaced from the selecting nucleic acid molecules affixed to the column.

Alternatively, selection of RNA aptamers can be carried out using a gel-shift assay, wherein the selecting nucleic acid molecule is detectably labelled and non-denaturing gel electrophoresis is used to separate non-complexed RNA from the RNA aptamer:selecting nucleic acid complex. Preferably, the RNA aptamer:selecting nucleic acid complex is electroeluted, and components are dissociated using dialysis.

The present invention facilitates the identification of a predominant RNA family, containing one or more characteristic sequence motifs. Individual sequences in RNA family so identified may fold into similar secondary structures.

Since RNA aptamers apparently bind to their cognate RNAs by shape recognition, they might serve as useful reagents for the study of RNA structure, function and dynamics. In this regard they would be analogous to protein antibodies and their recognition of biomolecules. While antibodies directed solely against RNA are rare, the methods of combinatorial selection and counterselection described here should allow RNA species capable of RNA recognition to be generated with relative ease.

BRIEF DESCRIPTION OF THE DRAWINGS

FIG. 3. Sequence analysis of aptamer RNAs: (a) the most abundant class of cloned sequences (SEQ ID NOS:2–7); (b) other sequences (SEQ ID NOS:8–9) present after 18 rounds of selection using Protocol G. Dots in (a) represent nucleotides identical to those shown at the corresponding position in the consensus sequence.

DETAILED DESCRIPTION

Figure 1A:
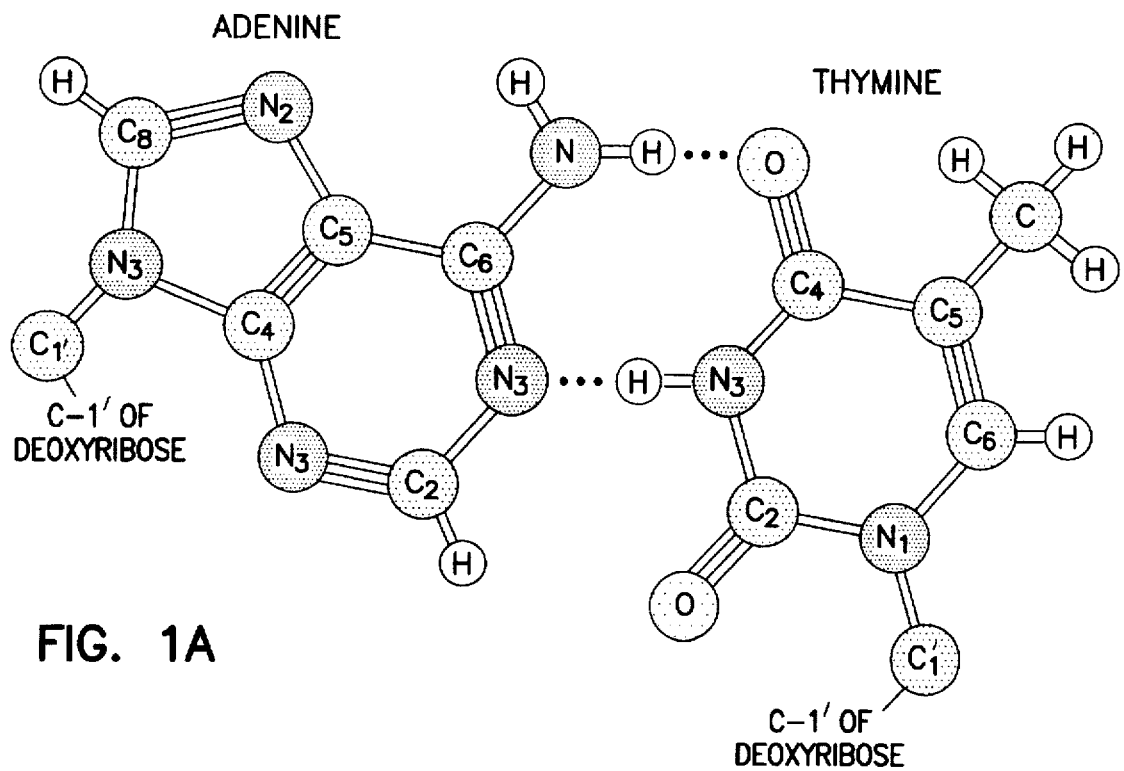
FIG. 1. Schematic representation of Watson-Crick base pairing.

The present invention provides a method for obtaining an RNA aptamer that recognizes another nucleic acid molecule, preferably an RNA molecule, by shape selection. The term "RNA aptamer" is used in the art to describe an RNA molecule capable of binding another molecular species. The method of the invention employs combinatorial RNA selection to identify, from a candidate RNA population, an RNA aptamer that binds a selecting nucleic acid structural element through mechanisms other than duplex- or triplex-type base pairing. The invention is particularly directed to a method of obtaining RNA aptamers that bind other RNA molecules.

The RNA aptamers of the invention recognize nucleic acid structural elements by means of shape recognition or selection. Structural elements are common in RNA molecules but are also found in DNA molecules. Such elements are typically defined in terms of secondary structures, which are produced by means of intramolecular Watson-Crick interactions and are characterized by local structures such as hairpins, stem-loops, bulge-loops, pseudoknots, and the like. However, the shape of structural elements may also be a product of tertiary, or long-range, interactions that may, but need not be, the result of Watson-Crick base pairing, such as tetraplex structures and G-quartets.

An RNA aptamer identified using the method of the invention can include a plurality of RNA molecules that bind the selecting RNA structural element.

Deoxyribonucleic acids (DNA) are formed by linear strings of the nucleotide bases adenine (A), thymine (T), guanine (G) and cytosine (C). In ribonucleic acids (RNA), uracil is used in place of thymidine. Watson-Crick base pairing is characterized by highly specific hydrogen bonding interactions (FIG. 1) between A and T(U), and between C and G, along complementary strands of nucleic acid to form a hydrogen bonded duplex. All nucleic acid sequences disclosed herein are written in the conventional 5' to 3' direction.

In a preferred embodiment of the invention, an RNA molecule containing the selecting structural element upon which the selection is based is synthesized, and the resulting selecting RNA molecule is brought into contact with a candidate RNA population. Typically, the selecting RNA molecule is prepared by in vitro transcription of a synthetic DNA or cDNA.

The present invention accomplishes a selection of an RNA aptamer from an candidate RNA population suspected of containing an RNA aptamer that binds to the preselected structural element of interest. Preferably, the RNA population is prepared from a randomized synthetic library. However, naturally occurring or recombinant RNA populations can be used as well. In a preferred embodiment, a random synthetic library of DNA, constructed, for example, by the method of Ellington et al. (*Nature*, 346, 818–822 (1990)), is transcribed, and the resulting RNA population is assayed for binding to the target structural element. Preferably, the RNA populations contains at least about $10^6$ unique sequences, more preferably at least about $10^{13}$ unique sequences.

In a particularly preferred embodiment of the invention, each of the members of the RNA population contains a synthetic randomized sequence of preferably between about 20–100 nucleotides, more preferably between about 40–70 nucleotides, flanked or bounded at the 3' end and 5' end by a commonly shared nucleotide sequence such as that for the T7 promoter (see Example).

Prior to selection, members of the RNA population having nucleotide sequences that would enable them to form base pairing duplexes or triplexes with the selecting RNA molecule are essentially removed from the population. This is done to insure that an RNA molecule that binds the selecting structural element according to the method of the invention recognizes the shape of the structural element and does not interact therewith solely by way of Watson-Crick or other helix forming base pairing interactions. The method of the invention preferably selects RNA aptamers that form non-covalent complexes with selecting nucleic acid structural elements resulting from binding interactions that substantially exclude duplex- or triplex-type base pairing interactions. The binding population is thus enriched for those RNA molecules in the candidate RNA population that are capable of tertiary interaction (i.e., shape selection) with the selecting RNA structural element.

Preferably, RNA molecules having nucleotide sequences capable of base pairing with the selecting structural element are removed from the RNA population by duplexing them with a synthetic blocking oligodeoxynucleotide. The blocking oligodeoxynucleotide has a nucleotide sequence equivalent to that of the selecting structural element. A blocking oligodeoxynucleotide having a nucleotide sequence that differs from the nucleotide sequence of the structural element by only an insignificant number of substitutions, deletions or additions, such that duplex formation is not impaired relative to an oligodeoxynucleotide sequence that is 100% identical to that of the structural element, is considered to have a nucleotide sequence equivalent to that of the structural element. The blocking oligodeoxynucleotide is thus expected to form duplexes with complementary RNA molecules present in the RNA population used as the starting material in the method of the invention. When the structural element is RNA rather than DNA, the equivalent blocking oligodeoxynucleotide has the nucleotide sequence of the structural element except that T is used in place of U.

The blocking oligodeoxynucleotide may be a single oligodeoxynucleotide or it may include a plurality of overlapping oligodeoxynucleotide. Preferably, each overlapping oligodeoxynucleotide of the plurality of overlapping oligodeoxynucleotides contains at least 20 nucleotides and has a nucleotide sequence equivalent to a portion of the structural element, such that each nucleotide position in the structural element corresponds to a nucleotide position in at least one of the overlapping nucleotides. Use of a plurality of overlapping nucleotides is preferable because it will block potential duplex- or triplex- type base pairing interactions of RNA molecules that would otherwise have paired with only a portion of the structural element. The shorter overlapping oligodeoxynucleotides may thus more effectively block out undesirable intramolecular base pairing interactions than an oligodeoxynucleotide comprising a nucleotide sequence equivalent to the entire sequence of the structural element.

The RNA library and the blocking oligodeoxynucleotide are reacted together for a time and under buffer conditions sufficient to allow duplex formation. Preferably, the buffer contains about 1–100 mM $Mg^{2+}$, more preferably about 20–50 mM $Mg^{2+}$.

Preferably, the combinatorial RNA chemistry employed by the method of the invention is SELEX (SELEX: Systematic Evolution of Ligands by Selective Enrichment, C. Tuerk et al., *Science*, 249, 505–510 (1990)). Multiple generations of selection/amplification yield an ensemble of selected sequences which can be analyzed for conserved sequence motifs, e.g., by the Gibbs sampler program of Lawrence, et al., *Science*, 262, 208–214, (1993).

Bound RNA is separated from the bulk (free) RNA population by any convenient separation method. Preferably, affinity chromatography or a gel-shift assay is used. Membrane binding and separation schemes based on biotin/avidin interaction are examples of other suitable separation methods.

When affinity chromatography is used, the selecting RNA molecule is affixed to a column matrix. Preferably, the matrix material chosen will exhibit minimal nonspecific binding to RNA molecules present in the candidate RNA population. The selecting nucleic acid molecule, which may include an activated functional group, can be covalently linked to a suitable matrix material. Direct covalent linkages or linkages mediated by linker molecules may be used. For example, an oxidized selecting RNA molecule may be coupled to a Sepharase-adipic acid hydrazide resin by way of hydrazone formation. Alternatively, the selecting nucleic acid may be affixed to the matrix using noncovalent linkages, such as that formed between biotin and avidin. For example, the selecting nucleic acid can be biotinylated, and the biotinylated nucleic acid can be affixed to a column matrix comprising avidin molecules.

The candidate RNA population is incubated with matrix-bound selecting nucleic acid. This incubation occurs in a buffer that allows the selecting RNA to bind members of the RNA population that recognize the shape of a structural element in the selecting RNA, forming a noncovalent RNA aptamer:selecting nucleic acid complex. Rinsing the matrix in buffer separates the unbound (free) members of the RNA population from those bound by the selecting nucleic acid molecule. Bound RNA is then dissociated from the RNA aptamer:selecting nucleic acid complex by a method that disrupts the binding interactions between the RNA aptamers and the selecting nucleic acid molecules.

Preferably, bound RNA is eluted from the column matrix by chelating the $Mg^{2+}$ present in the buffer solution. EDTA, EGTA, or a similarly effective chelating agent is preferably used. More preferably, the amount of chelating agent is equimolar with the amount of $Mg^{2+}$ in solution. Alternatively, bound RNA can be eluted by supplying an amount of competing nucleic acid effective to displace the bound RNA from the selecting nucleic acid molecule. In a particularly preferred embodiment, the nucleotide sequence of the competing nucleic acid comprises the nucleotide sequence of the structural element of the selecting nucleic acid molecule.

When a gel-shift assay is used, a quantity of selecting RNA molecule is labeled and is then mixed, along with a quantity of non-labeled selecting RNA molecule, with a candidate RNA population. Preferably, a radioactive label is used, but any suitable label may be used, such as a fluorescent tag, an enzyme label, or a biotin label.

The candidate RNA population and the labeled selecting nucleic acid molecule are incubated together in an appropriate buffer for a time sufficient to allow the formation of a labeled RNA aptamer:selecting nucleic acid molecule complex. Preferably, free RNA is resolved from the bound complex using a polyacrylamide gel. The percentage of polyacrylamide used will vary depending on the size of the molecules that need to be separated, and is well known in the art. Preferably a 6–8% polyacrylamide gel is used. After resolution, the position of the labeled complex is determined by detecting the label using an appropriate method of detection. The complex is removed from the gel by any convenient means, such as by excision followed by either electroelution or mechanical crushing and soaking. The bound RNA aptamers may be dissociated from the selecting nucleic acid molecules, preferably in the presence of a chelating agent, using dialysis, filtration, or the like.

Preferably, multiple rounds of selection are used in the method of the invention. As the RNA population is subjected to further rounds of selection, the complexity, i.e., the number of different RNA sequences that make up the RNA population, will decrease. This decrease in complexity can be monitored. After any round of selection, the selected RNA aptamers may be reverse transcribed into cDNA, amplified, ligated into a plasmid, and then used to transform competent bacterial cells according to methods well known in the art. Plasmid DNA can be isolated from the resulting colonies and the nucleotide sequence of the insert DNA that is encoded by the reverse transcribed RNA can be determined. Alternatively, nucleotide sequences of the selected RNA population can be determined directly using polymerase-chain-mediated DNA sequencing techniques well known in the art. As the RNA population is subjected to further rounds of selection, the numbers of different nucleotide sequences that result from DNA sequence analysis of the aptamer DNA will decrease.

Applications of this invention include any instance where the tertiary structure of a nucleic acid needs to be detected or targeted. An RNA aptamer identified using the method of the invention can be expected to have various clinical and scientific utilities that depend, in part, on the selecting RNA structural element used to isolate it. Some of the many potential utilities of RNA aptamers thus identified include their use as laboratory, diagnostic, or therapeutic reagents, as components of genetically engineered ribozymes (RNA enzymes), and as template compounds for rational drug design.

For example, RNAs which are capable of binding to RNAs in a structure-dependent fashion can be used in a diagnostic or therapeutic context to identify or to interfere with the translation of messenger RNAs that encode a deleterious protein. In the absence of the present invention there is currently no way to target mRNAs in a cell except by utilizing antisense RNAs which bind to their cognate messenger RNAs in a sequence-dependent (i.e., Watson-Crick base pairing) fashion. However, the use of antisense RNAs for targeting mRNAs in cells is kinetically limited in that the cognate RNAs must be unfolded to present complementary sequences for binding. This can be a slow process, leading to incomplete recognition or control of gene activity. Structural recognition of mRNA using RNA aptamers selected in accordance with the method of the invention would not be kinetically limited in this fashion.

Moreover, structures of RNA aptamers that recognize the shape of a selecting RNA of interest could be determined by spectroscopy or X-ray crystallography. These structures could be used to guide the rational design of mimetics that would recognize and bind to specific cellular RNAs, much as known aminoglycoside antibiotics bind to a defined domain or ribosomal RNAs in effecting their antimicrobial action.

As another example, catalytic RNAs could be synthesized using a binding domain composed of shape-recognizing RNA selected by the method of the invention and a catalytic domain derived from a known ribozyme or synthesized de novo. These catalytic RNAs could be used to target cellular RNAs for cleavage. This technology could be used for genetic control in recombinant organisms, or therapeutically. Further, recognition of substrates by catalytic RNA has until now been based on the motifs present in naturally-occurring ribozymes. The present invention allows for the identification of RNA aptamers to RNA domains that are not yet known to occur in nature.

RNA aptamers identified in accordance with the method of the invention can also be used to identify conserved RNA structures in the absence of sequence homology. For example, viral RNA sequences typically change during a single infective event or epidemic in response to immune challenge. Structural analysis of RNAs can be used in diagnostics where, e.g., mutant viral RNAs are be analyzed for the presence of a particular RNA three-dimensional structure important for the viral life cycle. In retroviruses, for example, including HIV, a particular RNA three-dimensional structure is required for translation frameshift. The particular RNA sequence is less important than the three-dimensional structure assumed by the nucleotide string. RNA aptamers identified using the method of the invention can be screened or tested for their ability to specifically inhibit frameshifting in vitro. RNA aptamers that inhibit frameshifting could potentially be used therapeutically or as a basis for rational drug design.

In clinical diagnostics, methods of hybridization may be insensitive to small changes in nucleotide sequence. However, small differences in nucleic acid sequence can lead to large differences in three-dimensional structure, and hence function, of an RNA. For example, Herlocher et al (*Proc. Nat'l. Acad. Sci.*, 90, 6032–6037 (1993)) proposed that silent nucleotide changes (i.e., base substitutions that do not change the sequence of the encoded protein) can lead to a variant three-dimensional structure in a cold adapted influenza virus that affects infectivity. In order to monitor such changes, a means of recognizing the three-dimensional structure of the viral RNA would be useful. The present invention offers a means for assessing subtle changes in sequence that significantly impact three-dimensional structure.

Evidence also exists that single stranded DNA is capable of forming hairpin structures. For example, nuclear magnetic resonance and gel electrophoresis indicate that the individual strands from the fragile X triple repeats form intramolecular hairpins under physiological conditions (Chen et al., *Proc. Natl. Acad. Sci. USA*, 92, 5199 (1995)). The ability of single stranded DNA to form hairpins has been proposed to play a critical role in the large scale expansion of dinucleotide and trinucleotide repeats present in genetic diseases including Huntington's disease, fragile X, myotonic dystrophy, spinocerebellar ataxia type 1, hereditary dentatorubral-pailidoluysian atrophy and colon cancer tumors (Gacy et al., *Cell*, 81, 533 (1995)). Consequently, the ability to isolate RNA aptamers that bind these DNA structural motifs could be used in diagnostic applications to identify individuals expressing these DNA structural motifs or potential therapeutic applications to treat individuals suffering from these syndromes.

The invention is not limited to any particular scientific theory regarding binding mechanism or mode of interaction used by the selected RNA aptamer, the binding site of the RNA aptamer on the selecting RNA, or the level of binding specificity of the RNA—RNA interactions based upon which the selection is made.

The invention will be further described by reference to the following detailed example.

EXAMPLE

RNA Aptamer Selection and Characterization

Synthetic RNA library. RNA aptamers capable of binding a small stem-loop domain from *Bacillus subtilis* ribonuclease P (RNase P), nucleotides 61–80 (FIG. 2), were selected using a synthetic RNA library containing strings of 50 randomized nucleotides bounded by the promoter sequences
AGTAATACGACTCACTATAGGGAGAAT-TCCGACCAGAAG (SEQ ID NO:11) and
TGAGGATCCATGTAGACGCACATA (SEQ ID NO:12) at the 5' and 3' ends, respectively. The synthetic RNA library was a gift of Prof. A. D. Ellington (Indiana University). This particular target ligand was chosen because non-Watson-Crick RNA—RNA interaction is known to occur during substrate recognition by RNase P RNA.

The RNA library was amplified through 5 cycles of polymerase chain reaction (PCR). Similar PCR conditions were used throughout the experiment. Taq polymerase was purchased from Fisher Biotech, Pittsburgh, Pa., and used according to the manufacturer's directions. The PCR reaction mixture typically contained 5% acetamide, 0.05% NP40 detergent, 200 µM each of the four deoxyribonucleotides (dNTPs), 0.5 µM primer, 5 units Taq polymerase, approximately 0.1 µg target DNA, in a volume of 100 µL. The reaction cycle used was 94° C. for 1 minute, 45° C. for 1 minute, 72° C. for 2 minutes, followed by a 5 minute final extension at 72° C.

One microgram of this resulting DNA population was transcribed with T7 RNA polymerase (Epicentre Technologies, Madison Wis.) in a 20 µL reaction according to the manufacturer's directions. Transcripts were purified by gel electrophoresis through denaturing polyacrylamide gels (7M area in Tris-borate-EDTA buffer). The purified RNA library (30 µg) in 0.1 mL 10 mM TrisCl, pH 8.0/100 mM NaCl (Sigma Chemical Co., St. Louis, Mo.) was brought to 70° C. for 10 minutes and slowly cooled to room temperature. The solution was then made 25 mM in $MgCl_2$. Buffer conditions supporting substrate recognition by RNase P RNA, i.e., $[Mg^{2+}]=25$ mM and moderate ionic strength, ($\mu=0.34$), were used in the binding experiments.

Figure 2:
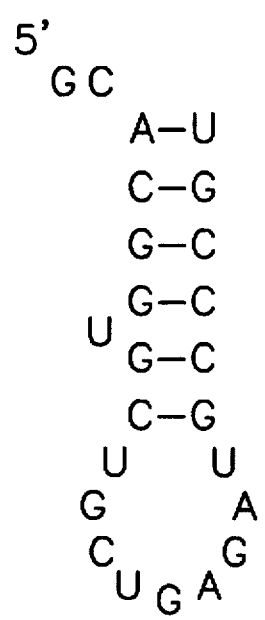
FIG. 2. Schematic representation of small stem-loop structure derived from nucleotides 61–80 of *Bacillus subtilis* P RNA (SEQ ID NO:1).

Blocking Oligodeoxynucleotide. While it might be expected that under the solution conditions employed in these experiments the folded structure of RNA species would present a substantial activation energy barrier to Watson-Crick base pair formation, this could not be ensured a priori. Thus, selection of sequences capable of forming extensive Watson-Crick base pairs with the selecting RNA structural element was avoided by using a blocking strategy to remove Watson-Crick-complementary molecules from the selectable pool of library RNAs (FIG. 2).

Specifically, a synthetic oligodeoxynucleotide of the same primary sequence as the RNA stem-loop was mixed in molar excess with the purified RNA library prior to the binding step. This oligodeoxynucleotide is expected to form the same Watson-Crick base pairs as the RNA stem-loop used for selection; its presence in the binding mixture therefore should remove complementary sequences from the selectable pool of RNAs in the library. On the other hand, since it lacks the 2'-OH functionality of RNA, the blocking oligonucleotide is not capable of forming the same tertiary interactions with RNA aptamers as would the stem-loop RNA. Therefore, it should not interfere with shape recognition between aptamer and stem-loop RNAs. The blocking oligonucleotide (GCACGGTGCTGAGATGCCCGT (SEQ ID NO:13), 2.6 µg), representing the DNA equivalent of the RNA stem-loop sequence described above, was added and the mixture was kept at room temperature for 1 hour before selection.

Isolation of RNA aptamers. A selecting RNA having the stem-loop sequence of interest was synthesized by transcription from the oligodeoxynucleotide ACGGGCATCTCAG-CAGCACCGTGCTATAGTGAGTCGTATTAC (SEQ ID NO:14) to which the T7 promoter oligonucleotide AGTAATACGACTCACTATA (SEQ ID NO:15) had been annealed, according to the method of Milligan, et al., (incorporated herein in its entirety) (J. F. Milligan et al., *Nucl. Acids Res.*, 15, 8738–8798, (1987)). The resulting RNA stem-loop had the nucleotide sequence GCACGGUGCUGCUGAGAUGCCCGU(SEQ ID NO:1).

Two separate protocols were used to isolate RNA aptamers capable of binding the stem-loop structures. Protocol "A" used affinity column chromatography, and protocol "G" used a gel-shift assay, to separate bound aptamers from non-binding RNA fragments. Both protocols A and G were initially carried out through 12 generations of SELEX, as described below. Protocol G was continued for a total of 18 generations of SELEX. After each round, the selected RNAs were recovered, reverse-transcribed (Superscript I, Bethesda Research Laboratories, Gaithersburg, Md.) to generate complementary DNAs (cDNAs), and the cDNAs were amplified by 10 cycles of PCR. Transcripts of the PCR product were used for the next round of selection.

Protocol A: Affinity Column Chromatography. A quantity of the stem-loop sequence (145 µg), was dissolved in 100 µL of 0.1 M potassium phosphate, pH 8.0. The stem-loop RNA was oxidized at its 3' end by adding 50 µL of freshly prepared, ice-cold 20 mM $NaIO_4$ (Fluka Chemical, Ronkonkoma, N.Y.) and keeping the solution on ice in the dark for 2 hours. The RNA was recovered by ethanol precipitation and redissolved in 0.1µL of 0.1M potassium acetate, pH 5.0. The oxidized RNA was coupled via hydrazone formation to 0.5 mL of packed Sepharose-adipic acid hydrazide resin (Pharmacia, Piscataway, N.J.) at 4° C. overnight, with gentle mixing, to produce an RNA-coupled resin. Efficiency of coupling was determined to be >95%.

The RNA library was preselected through a column (0.5–1 mL bed volume) of Sepharose-adipic acid hydrazide in P buffer (P buffer: 10 mM TrisCl, pH 8.0/100 mM NaCl/25 mM MgCl$_2$) to remove any RNAs that bound non-specifically to the column matrix. The preselected RNAs were then applied to the affinity column (0.5 mL bed volume) of RNA-coupled resin. The affinity column was washed with 5 mL of P buffer, then the bound RNA population was eluted by reducing the ionic strength and chelating the Mg$^{2+}$ out of solution using 2 column volumes of 25 mM Na-EDTA, pH 8.0. The eluted RNA was recovered by ethanol precipitation using 200 μg glycogen (Sigma Chemical Co., St. Louis, Mo.).

Protocol G: gel-shift assay. A quantity of stem-loop RNA was uniformly labeled with [α-$^{32}$P] CTP (New England Biolabs, Boston, Mass.) during transcription. Purified library RNAs were preincubated in 10 mM Tris-Cl, pH 8.3/25 mM MgCl$_2$/100 mM NaCl/165 mM KCl at 70° C. for 10 minutes in the presence of a known concentration of labeled stem-loop RNA and cooled to room temperature. The reaction mixtures were loaded on a 6% or 8% non-denaturing polyacrylamide gel in E buffer (E buffer: 100 mM Tris-HEPES, pH 8.3/1 mM MgCl$_2$/1 mM KCl/0.1 mM EDTA).

Complexed RNA species migrated more slowly than free stem-loop RNAs. The region of the gel corresponding to slowly migrating complexes was excised, and the complexed RNA was electroeluted from the gel by electrophoresis into a dialysis bag and dialyzed. The RNA was received by ethanol precipitation using 200 μg glycogen. (The retarded band comprising the complexed RNA was not visible by autoradiography during the early cycles.)

DNA transformation, cloning and sequencing. Amplified cDNA fragments were digested with EcoR1 and BamH1 and ligated (T4 ligase, Bethesda Research Laboratories, Gaithersburg, Md.) into plasmid pGEM-3Z (Promega Biotech, Madison, Wis.) according to the manufacture's direction. Transformation was into INVαF' competent cells (Invitrogen Corporation, San Diego, Calif.) or DH5α. Plasmid DNAs were prepared with a modified mini alkaline-lysis/PEG precipitation protocol (Applied Biosystems, Foster, Calif.). Sequences of the inserted fragments were determined by the chain-termination method using Sequenase version 2.0, United States Biochemical, Cleveland, Ohio).

DNA sequence analysis. DNA sequence analysis, including database searching and structure prediction, was performed using the GCG software package (Genetics Computer Group, Madison Wis). The Gibbs sampler program of Lawrence et al. (D. E. Lawrence et al., *Science*, 262, 208–214, (1993)) was implemented at the Pittsburgh Supercomputing Center, as were the programs used to analyze the Gibbs sampler output.

After 12 generations of SELEX, analysis of the sequence complexity of the populations using the GCG PileUp program revealed that most of the sequences were not closely related. Further, the full sequences of the RNAs in the sequence ensemble derived from protocol A (12 generations) were as related to the full sequences of the RNAs in the sequence ensemble derived from protocol G (12 generations) as they were to each other. Thus no single selected sequence was dominant in the populations selected through 12 rounds of either protocol.

In order to determine whether any shorter subsequences were conserved in the binding populations, the sequence ensemble from Protocol G was analyzed using the Gibbs sampler program. Local increases in information per parameter were found corresponding to three particular sequences (3, 6, and 12 nucleotides long, respectively), indicating the presence of selected motifs of these lengths. The best fitting sequences were RYA, AgctGC, and gctGCcTGgtcA (SEQ ID NO:16), respectively, with capitalized positions being most informative and where R=A or G, and Y=C or T/U.

To determine the significance of these selected sequence motifs, the individual aptamer sequences in the ensemble were randomized and reanalyzed. In 100 separate trials, trimers of equal or greater information content were found twice, hexamers were found four times, and dodecamers were not found. Thus, the observed motifs were not simply the adventitious result of a biased base composition in the selected RNAs. The probability of the motifs not occurring by chance was significant in all cases but most significant for the dodecamer.

As stated above, protocol G was continued for a total of 18 generations of SELEX. At this time, DNA sequence analysis of the bulk population indicated that the clones were closely related. Individual selected molecules were cloned and the sequences determined. Five of seven sequences determined were closely related. (FIG. 3(a)).

A single predominant sequence was identified after 18 generations of SELEX. It is highly significant that this winning sequence was found in earlier populations (12 generations) selected either by affinity chromatography or gel-shift experiments. This observation also argues against the winning sequence being an artifact of the selection process (for example, a matrix-binding aptamer).

A search for the g18_1.1 (SEQ ID NO:5) sequences in the RNA ensemble identified after 12 rounds of SELEX indicated that one related clone was present in the populations derived by each of protocols A or G. A FASTA (GCG) search of the GenBank database, Release 92, did not identify any homologous sequences.

Sequences g18_01 (SEQ ID NO:2), g18_04 (SEQ ID NO:3), g18_10 (SEQ ID NO:4), g18_11 (SEQ ID NO:5) and g18_12 (SEQ ID NO:6) in FIG. 3(a) were isolated through 18 rounds of selection by protocol G. (E. S. Haas et al., *Science*, 254, 853–856, (1991)). The sequence of the g18_11 (SEQ ID NO:5) transcript has been deposited in GenBank under accession number 634759. Sequence g12_3 (SEQ ID NO:7) was derived through 12 rounds of selection by protocol G, while sequence a_07 (SEQ ID NO:5) was derived through 12 rounds of affinity column selection (protocol A). We concluded that the sequence family shown in FIG. 3(a) (SEQ ID NOS:2–7) represents a locally optimal solution to the problem of RNA—RNA interaction and that its selection was independent of the protocol used. Searches for the predicted hexamer in the consensus RNA indicated that the hexamer was strongly conserved in this sequence (beginning at nucleotide 38 in the sequences shown in FIG. 3(a)). The dodecamer (SEQ ID NO:16) was less strongly conserved; however, two copies related to this sequence were found beginning at nucleotides 18 and 39, respectively.

The selected RNA population (FIG. 3(a)) (SEQ ID NO:2–7) consisted of molecules whose longest contiguous stretch of Watson-Crick complementarity with the selecting stem-loop RNA used for selection was 4 nucleotides. This extent of complementarity is well within the extent predicted to occur between two random sequences 24 and 50 nucleotides long. To illustrate, consider that the 50-mer sequence imbedded in the aptamer RNA represents 20 percent of all possible tetrameric sequences. The probability of not finding a given tetramer is thus 0.80. There are 18 different tetrameric subsequences in the 21-nucleotide selecting RNA sequence. Therefore, the probability of not finding any matches of length 4 between the two sequences is $(0.80)^{18}$= 0.02; i.e., there is a 98% probability of this degree of complementarity occurring by chance. This probability rapidly increases as the region of complementarity searched for becomes longer so that, e.g., the probability of not finding a 6-nucleotides match in two random sequences of this size is 0.77.

The regions of Watson-Crick complementarity between the predominant g18 RNA species and the selecting stem-loop include portions of both the stem and loop of the RNA used for selection, further suggesting that the interaction between the two RNA molecules is not solely due to Watson-Crick interaction. Since the loop would be expected to be most available for Watson-Crick binding, this further argues that Watson-Crick base pair formation is not the sole mode of interaction between the molecules.

Additionally, the selection of a predominant molecule after 18 rounds of selection argues that the interaction does not involve short regions of Watson-Crick interaction. These sequences would be represented many times in the library. Even a 16-mer would be present >2000 times in a library of $10^{31}$ members and a significant fraction of those should present complementary regions in a structural context available for binding. Further, if Watson-Crick complementary sequences were the sole means of interaction, then the Gibbs sampler analysis would be likely to identify them as conserved motifs during intermediate rounds of selection. This did not occur; the conserved motifs identified after 12 generations of SELEX were not complementary to the stem-loop used for selection. This argument does not rule out the possibility of local Watson-Crick hydrogen bonding contributing to the interaction between the RNAs, but it means that Watson-Crick interaction is not the sole determinant of binding.

Figure 4:
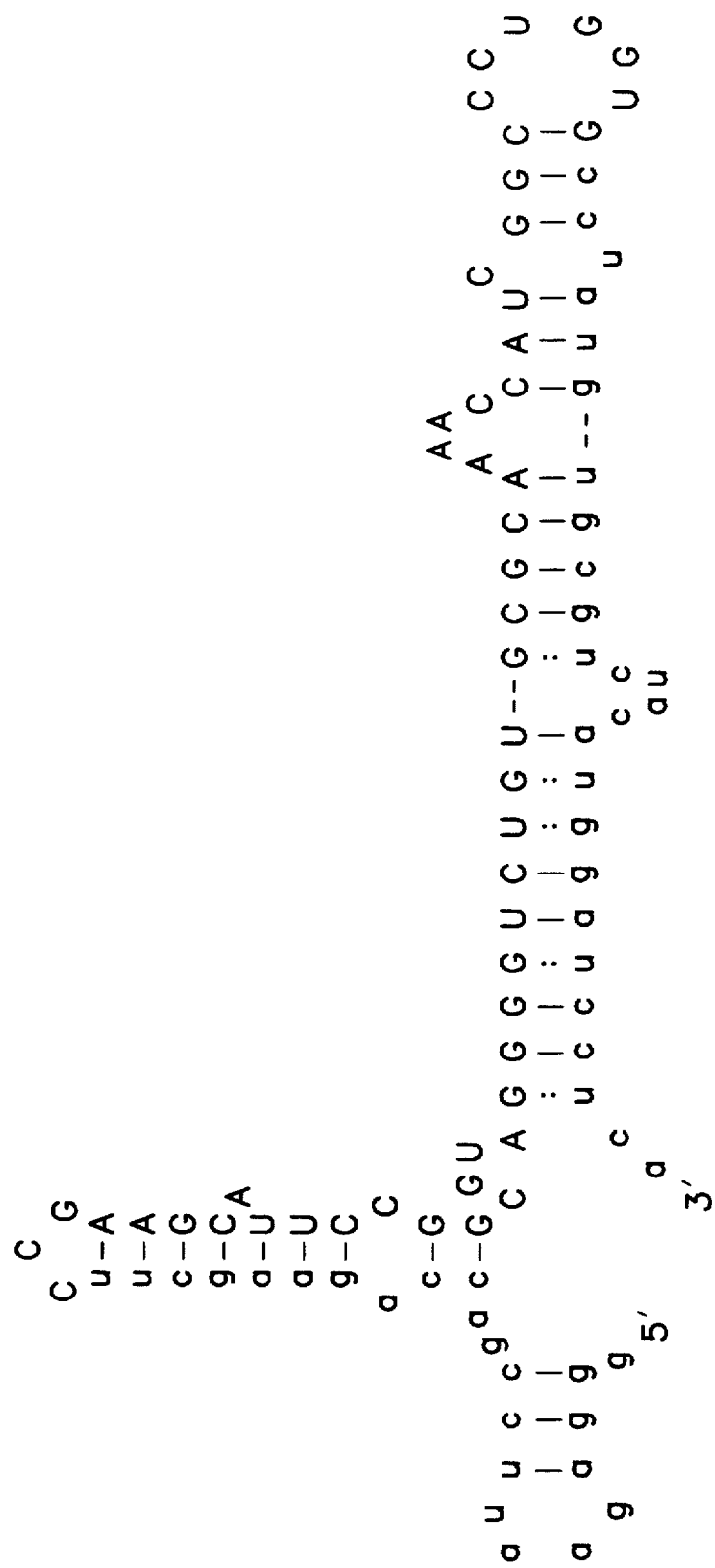
FIG. 4. Schematic representation of a possible secondary structure of RNA aptamer g18_04 (SEQ ID NO:10).

An optimal predicted secondary structure of the consensus RNA (g18__11)(SEQ ID NO:5), including the flanking sequences 5' and 3' to the 50 nucleotide sequence shown in FIG. 3(a), is shown in FIG. 4. Primer sequences at the 3' and 5' ends of the transcript are indicated in lower case and the unique portion of the molecule is indicated in capitals. Each of the sequences in FIG. 3(a)(SEQ ID NOS: 2–7) is predicted to fold into a similar secondary structure with a ΔG of formation within 2.0 kcal of the optimal folding. This structure was found by the MFOLD program (M. Zuker, Science, 244, 48–52 (1989)) to have a predicted folding energy within 2.0 kcal (4.4 kJ) of the optimal folding for each of the sequences in FIG. 3(a). (SEQ ID NOS:2–7). The structure in FIG. 4 was also consistent with nuclease digestion studies.

Sequences g18__06 (SEQ ID NO:8) and g18__09 (SEQ ID NO:9)(FIG. 3(b)) were present after 18 rounds of SELEX. Selection of these sequences may be the result of Watson-Crick complementary interactions between these RNAs and the stem-loop sequence used for selection. The sequence of g18__06 (SEQ ID NO:8) contained stretches of 6 and 7 nucleotides, separated by 3 nucleotides, capable of Watson-Crick base-pairing to the selecting RNA stem-loop. Sequence g18__09 (SEQ ID NO:9) contained 5 contiguous residues complementary to the loop of the RNA used for selection.

Binding constants. RNA—RNA binding constants ($K_d$) were estimated by gel electrophoretic mobility shift. The inserted sequences of plasmid constructs including the T7 promoter region were amplified by PCR and transcribed using T7 RNA polymerase (Ampliscribe, Epicentre, Madison, Wis.). A tracer amount of stem-loop RNA was uniformly labeled with $|\alpha\text{-}^{32}P|$ CTP during transcription. Aptamer RNAs (g18__04) at different concentrations were incubated in B buffer (B buffer: 10 mM Tris-Cl, pH 8.3/25 mM $MgCl_2$/100 mM NaCl/165 mM KCl) at 70° C. for 10 minutes in the presence of a fixed concentration of radiolabeled stem-loop RNA and slowly cooled to 4° C. The samples were applied to a 6% polyacrylamide gel which had been prerun overnight in E buffer. Electrophoresis was in E buffer at a constant voltage of 100 V. Formation of the RNA—RNA complex resulted in the electrophoretic retardation of the radioactive ligand. Quantitation of free and complexed stem-loop RNA was performed by autoradiography and Beta scanning (Molecular Dynamics, Sunny Vale, Calif.). Binding constants were estimated assuming a single-site binding model.

Figure 5:
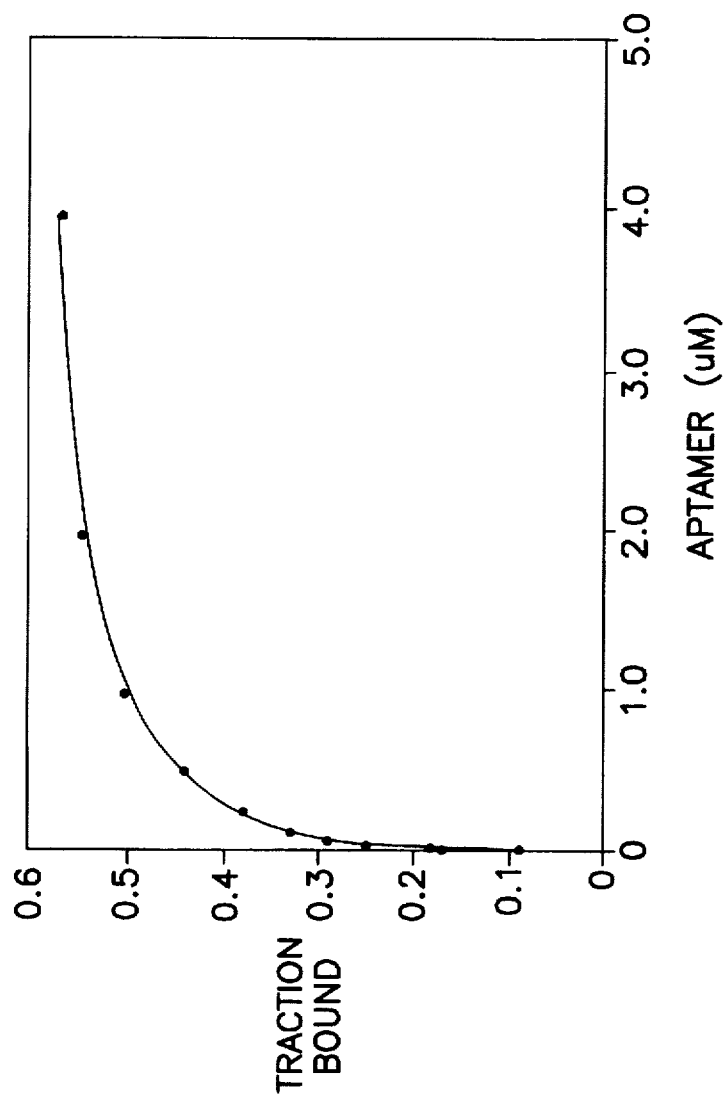
FIG. 5. Graphical representation of binding of RNA aptamer g18_04 (SEQ ID NO:10) to radioactive stem-loop RNA.

A graphical analysis of the binding data is shown in FIG. 5. The data were fitted to the sum of two hyperbolae with an overall R value greater than 0.998. The first fitted Kd was 70+/−15 nM and the second Kd was 4.4+/−1.1 μM. The first $K_d$ likely represents specific binding of the stem-loop and aptamer RNA, while the second represents a nonspecific interaction of the RNAs. Nonspecific interactions were confirmed in additional experiments that indicated that the aptamer RNAs aggregated at concentrations near 10 μM. This aggregation could also account for the observed failure of the binding reaction to go to completion; complete binding between the two RNAs was not attainable since the activity of the aptamer RNA was determined by its state in solution.

A similar $K_d$ value was determined for association of g18_01 RNA with the stem-loop RNA. The apparent $K_d$ between RNA aptamer g18$_{13}$04 and the stem-loop RNA was 70 nM under solvent conditions typical for catalysis by RNase P RNA. This affinity is similar to the interaction of RNase P RNA with its pre-tRNA substrate, for which the $K_m$ is 50 nM at 37° C. (D. Labuda et al., Nucl. Acids Res, 13 3667–3683, (1985)). The extent of binding was not affected by the presence of blocking oligodeoxynucleotide in molar excess to the aptamer RNA; this observation further supported the contention that the interaction between aptamer and stem-loop RNAs was not a result of Watson-Crick interaction.

All publications, patents and patent documents cited herein are incorporated by reference herein, as though individually incorporated by reference. The invention has been described with reference to various specific and preferred embodiments and techniques. However, it should be understood that many variations and modifications can be made while remaining within the spirit and scope of the invention.

What is claimed is:

1. A method for obtaining an RNA aptamer that binds a structural element of a selecting nucleic acid molecule comprising:

(a) contacting an RNA population suspected of containing an RNA aptamer that binds the structural element with an amount of blocking oligodeoxynucleotides, each having a nucleotide sequence equivalent to the nucleotide sequence of the structural element, for a time and under buffer conditions sufficient to allow duplex formation between the blocking oligodeoxynucleotide and all members of the RNA population having a sequence complementary to that of the blocking oligodeoxynucleotide, to yield a candidate RNA population comprising free RNA molecules and blocked RNA-oligodeoxynucleotide duplexes;

(b) contacting the candidate RNA population with the selecting nucleic acid molecule for a time and under buffer conditions sufficient to allow the formation of a noncovalent complex comprising bound RNA and the selecting nucleic acid molecule;

(c) separating non-complexed RNA from the noncovalent complex;

(d) separating the bound RNA from the selecting nucleic acid molecule of the noncovalent complex to yield a selected RNA population; and (e) repeating steps (b) through (d), wherein step (b) in the repetition is performed on the selected RNA population, for a number of cycles sufficient to yield a selected RNA population comprising a detectable amount of RNA aptamer.

2. The method of claim 1 wherein step (d) further comprises reverse transcribing the selected RNA population to yield a selected cDNA population; amplifying the selected cDNA population to yield an amplified selected cDNA population; and transcribing the amplified selected cDNA population to yield an amplified selected RNA population; and wherein step (b) in the repetition is performed on the amplified selected RNA population.

3. The method of claim 2 wherein the RNA population of step (a) is a synthetic RNA library.

4. The method of claim 3 wherein the synthetic RNA library comprises at least about $10^6$ different RNA molecules.

5. The method of claim 4 wherein the synthetic RNA library comprises at least about $10^{13}$ different RNA molecules.

6. The method of claim 2 wherein each RNA molecule of the synthetic RNA library comprises a different nucleotide sequence of between about 20–100 nucleotides.

7. The method of claim 6 wherein the unique nucleotide sequence is between about 40–70 nucleotides.

8. The method of claim 6 wherein the unique nucleotide sequence of each RNA molecule is flanked on each of its 5' and 3' ends by a commonly-shared promoter nucleotide sequence.

9. The method of claim 2 wherein the structural element comprises a stem-loop structure.

10. The method of claim 2 wherein the selecting nucleic acid molecule is an RNA molecule.

11. The method of claim 10 wherein the structural element comprises a structure selected from the group consisting a hair pin structure, of a stem-loop structure, a bulge-loop structure, a pseudoknot, a tetraplex structure, and a G-quartet.

12. The method of claim 2 wherein the noncovalent complex formed in step (b) results from binding interactions that substantially exclude duplex- or triplex-type base pairing interactions.

13. The method of claim 2 wherein the amount of blocking oligodeoxynucleotides comprises a plurality of overlapping oligodeoxynucleotides, each overlapping oligodeoxynucleotide comprising at least 20 nucleotides and having a nucleotide sequence equivalent to a portion of the nucleotide sequence of the structural element, such that each nucleotide position in the structural element corresponds to a nucleotide position in at least one of the overlapping oligodeoxynucleotides.

14. The method of claim 2 wherein step (b) is performed in the presence of about 1–100 mM $Mg^{2+}$.

15. The method of claim 14 wherein step (b) is performed in the presence of about 20–50 mM $Mg^{2+}$.

16. The method of claim 2 wherein the nucleotide sequence of a member of the amplified selected RNA population is determined prior to step (e).

17. The method of claim 1 wherein the selecting nucleic acid molecule is affixed to a column matrix prior to step (b).

18. The method of claim 17 wherein step (d) further comprises eluting the bound RNA from the column in the presence of a chelating agent.

19. The method of claim 18 wherein step (b) is performed in the presence of about 1–100 mM $Mg^{2+}$, and wherein the chelating agent is about equimolar with the concentration of $Mg^{2+}$.

20. The method of claim 17 wherein step (d) further comprises eluting the bound RNA from the column with an amount of competing nucleic acid effective to displace the bound RNA from the selecting nucleic acid molecule.

21. The method of claim 20 wherein the nucleotide sequence of the competing nucleic acid comprises the nucleotide sequence of the structural element of the selecting nucleic acid molecule.

22. The method of claim 17 further comprising a preselection procedure performed prior to step (a), comprising (i) contacting the RNA population with the column matrix prior to attachment of the selecting nucleic acid molecule to the column matrix, for a time and under buffer conditions sufficient to allow the formation of an RNA:column matrix complex; (ii) separating the non-complexed RNA population from the RNA:column matrix complex to yield a preselected RNA population; and (iii) eluting the complexed RNA from the column matrix; and wherein step (a) is performed on the preselected RNA population.

23. The method of claim 1 wherein the selecting nucleic acid molecule is detectably labelled, and wherein step (c) further comprises using non-denaturing gel electrophoresis to separate non-complexed RNA from the noncovalent complex comprising bound RNA and a detectably selecting nucleic acid molecule.

24. The method of claim 23 wherein step (d) further comprises electroeluting the noncovalent complex from the gel and dialyzing the electroeluted noncovalent complex.

* * * * *

UNITED STATES PATENT AND TRADEMARK OFFICE
CERTIFICATE OF CORRECTION

PATENT NO. : 5,792,613

DATED : August 11, 1998

INVENTOR(S) : Francis J. Schmidt et al.

Figure 1B:
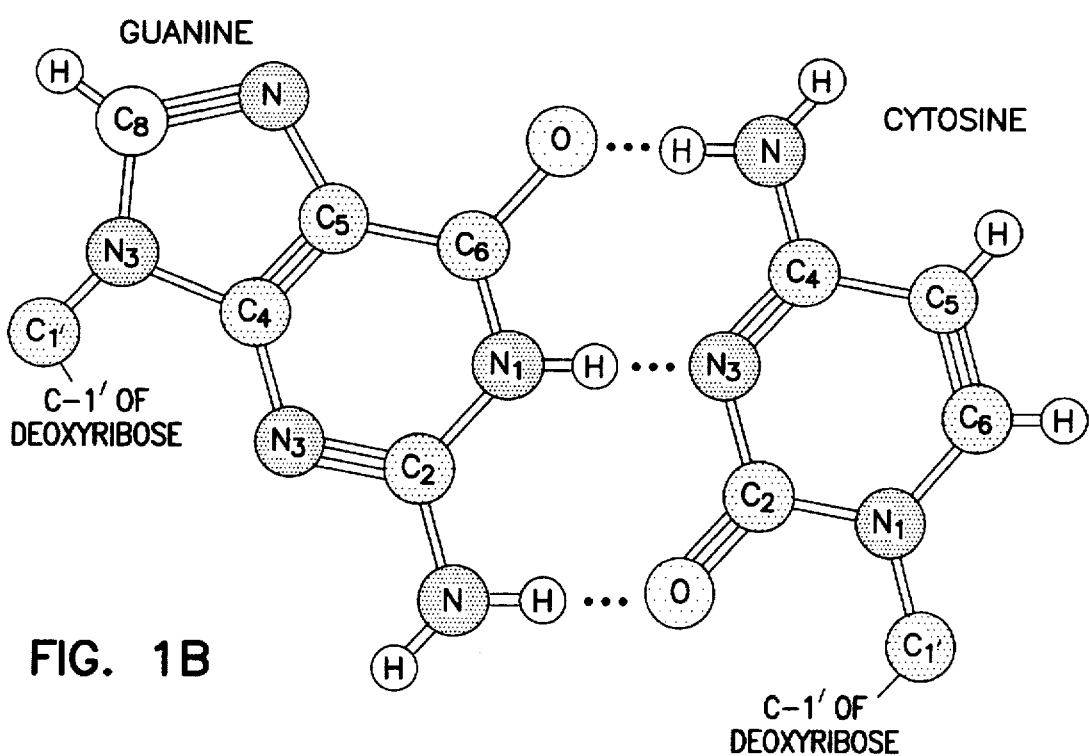

It is certified that error appears in the above-identified patent and that said Letters Patent is hereby corrected as shown below:

Column 4, line 20, delete "Figure 1" and insert therefor --Figures 1(a)-1(b)--.

Column 5, line 4, delete "Figure 1" and insert therefor --Figures 1(a)-1(b)--.

Signed and Sealed this

Twenty-third Day of February, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,792,613
DATED : August 11, 1998
INVENTOR(S) : Francis J. Schmidt et al.

It is certified that error appears in the above-identified patent and that said Letters Patent is hereby corrected as shown below:

At Col. 1, line 7, please delete "and" after "Foundation".

At Col. 1, line 8, please delete "Health." and insert --Health and Grant No. IR41AO38610-01 from the National Institute for Allergy and Infectious Disease.--.

At Col. 5, line 27, please delete "RNA populations" and insert --RNA population--.

At Col. 12, line 23, please delete "the g18_1.1" and insert --g18_11--.

At Col. 12, line 49, please delete "NO:2-7)" and insert --NOS:2-7)--.

At Col. 21, line 53, please delete "consisting a hair pin structure, of a" and insert --consisting of a hairpin structure, a--.

Signed and Sealed this

Thirteenth Day of July, 1999

*Attest:*

Q. TODD DICKINSON

*Attesting Officer*      Acting Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (i i) MOLECULE TYPE: mRNA (x i) SEQUENCE DESCRIPTION: SEQ ID NO:1:

GCACGGUGCU GCUGAGAUGC CCGU　　　　　　　　　　　　　　　　　　　　　　　　24

(2) INFORMATION FOR SEQ ID NO:2:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:2:

CCGAAGCATT CCGGCGTAGG GGTCTGTGCG CAAAACCATC GTCCCGGGTG　　　　　　50

(2) INFORMATION FOR SEQ ID NO:3:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:3:

CCGAAGCATT CCGGCGTAGG GGTCTGTGCG CAAAACCATC GGCCCTGGTG　　　　　　50

(2) INFORMATION FOR SEQ ID NO:4:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:4:

CCGAAGCATT CCGGCGTAGG TGTCTGTGCG CAAAACCATC GGCCCGGGTG　　　　　　50

(2) INFORMATION FOR SEQ ID NO:5:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:5:

CCGAAGCATT CCGGCGTAGG GGTCTGTGCG CAAAACCATC GGCCCGGGTG　　　　　　50

(2) INFORMATION FOR SEQ ID NO:6:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:6:

CCGAAGCATT CCGGCGTAGG TGTCTGTGCG CAAAACCATA GGCCCGGGTG          50

( 2 ) INFORMATION FOR SEQ ID NO:7:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:7:

CCGAAGCATT CCGGCGTAGG GGTCTGTGCG CAAAACTATC GGCCCGGGTG          50

( 2 ) INFORMATION FOR SEQ ID NO:8:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

TTCCTTAGGG GTTCAGTTGT TTCGCGCATG AACGGCATCA GTGCACCGTG          50

( 2 ) INFORMATION FOR SEQ ID NO:9:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

AGTTGATCGA GCGTGTTAGT TCTCCAATCT CTGTGTAGCG TGGAGCTGGG          50

( 2 ) INFORMATION FOR SEQ ID NO:10:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: mRNA ( x i ) SEQUENCE DESCRIPTION: SEQ ID NO:10:

GGGAGAAUUC CGACCAGAAG CUUCCGAAGC AUUCCGGCGU AGGGGUCUGU GCGCAAAACC          60

AUCGGCCCUG GUGCCUAUGU GCGUCUACAU GGAUCCUCA          99

( 2 ) INFORMATION FOR SEQ ID NO:11:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

AGTAATACGA CTCACTATAG GGAGAATTCC GACCAGAAG          39

( 2 ) INFORMATION FOR SEQ ID NO:12:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:12:

TGAGGATCCA TGTAGACGCA CATA                    24

( 2 ) INFORMATION FOR SEQ ID NO:13:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:13:

GCACGGTGCT GAGATGCCCG T                       21

( 2 ) INFORMATION FOR SEQ ID NO:14:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:14:

ACGGGCATCT CAGCAGCACC GTGCTATAGT GAGTCGTATT AC    42

( 2 ) INFORMATION FOR SEQ ID NO:15:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:15:

AGTAATACGA CTCACTATA                          19

( 2 ) INFORMATION FOR SEQ ID NO:16:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:16:

GCTGCCTGGT CA                                 12